United States Patent
Decker et al.

(10) Patent No.: US 6,955,744 B2
(45) Date of Patent: Oct. 18, 2005

(54) METHOD FOR PURIFYING 2-CHLORO-5-CHLOROMETHYLTHIAZOLE

(75) Inventors: Matthias Decker, Köln (DE); Dimitry Steinbach, Köln (DE); Torsten Taschner, Leverkusen (DE)

(73) Assignee: Bayer CropScience AG, Monheim (DE)

( * ) Notice: Subject to any disclaimer, the term of this patent is extended or adjusted under 35 U.S.C. 154(b) by 417 days.

(21) Appl. No.: 10/343,669

(22) PCT Filed: Jul. 30, 2001

(86) PCT No.: PCT/EP01/08789

§ 371 (c)(1),
(2), (4) Date: Feb. 3, 2003

(87) PCT Pub. No.: WO02/12209

PCT Pub. Date: Feb. 14, 2002

(65) Prior Publication Data

US 2004/0011639 A1 Jan. 22, 2004

(30) Foreign Application Priority Data

Aug. 10, 2000 (DE) .......................... 100 38 977

(51) Int. Cl.$^7$ .......................... B01D 3/34; C07D 277/32
(52) U.S. Cl. .......................... 203/63; 203/64; 203/100; 540/202
(58) Field of Search .......................... 203/91, 63, 64, 203/100; 540/202

(56) References Cited

U.S. PATENT DOCUMENTS 5,180,833 A   1/1993   Uneme et al. .............. 548/202
6,812,348 B1 * 11/2004  Hendel et al. .............. 548/202

FOREIGN PATENT DOCUMENTS

EP   780 384    * 12/1996
EP   763 531      3/1997
EP   794 180      9/1997
GB   1 083 910    9/1967

* cited by examiner

*Primary Examiner*—Virginia Manoharan
(74) *Attorney, Agent, or Firm*—Richard E.L. Henderson

(57) ABSTRACT

The present invention relates to a process for the preparation of pure 2-chloro-5-chloromethylthiazole by distillation in the presence of oligomeric polyethers.

14 Claims, No Drawings

METHOD FOR PURIFYING 2-CHLORO-5-CHLOROMETHYLTHIAZOLE

The present patent application has been filed under 35 U.S.C. 371 as a national stage application of PCT/EP01/08789, filed Jul. 30, 2001, which was published in German as International Patent Publication WO 02/12209 on Feb. 14, 2002, and is entitled to the right of priority of German Patent Application 100 38 977.5, filed Aug. 10, 2000.

The present invention relates to a process for preparing pure 2-chloro-5-chloromethylthiazole (CCMT) by distillation with addition of oligomeric polyethers.

CCMT is used, for example, as an intermediate in the preparation of insecticides. Accordingly, there is a need for preparing very pure CCMT in high yields.

EP-B 0 446 913 and EP-B 0 763 531 disclose the preparation of CCMT with subsequent purification by fractional distillation or purification by simple distillation and subsequent crystallization.

These processes have the disadvantage that, owing to the high boiling point, decomposition takes place even during the distillation of CCMT, resulting in a solid bottom which can no longer be handled. This can only be avoided by leaving sufficient CCMT in the bottom to keep it in the liquid state, resulting in reduced yields.

Furthermore, during fractional distillation, thermal stress is higher than during simple distillation, resulting in greater product loss owing to decomposition. In the case of the simple distillation, a subsequent recrystallization is required to achieve high product purity. This further process step causes an additional loss of yield via the mother liquor.

It was an object of the present invention to find an improved distillative purification process for CCMT.

Surprisingly, it has now been found that CCMT is obtained in very good yield and in very pure form when crude CCMT is distilled in the presence of an oligomeric polyether.

Accordingly, the present invention relates to a process for purifying CCMT, which is characterized in that CCMT is distilled in the presence of an oligomeric polyether.

Surprisingly, simple distillation of CCMT in the presence of an oligomeric polyether gives higher yields and a distillate of higher purity than without this additive. Moreover, because of the polyether additive, the bottom remains in the liquid state and can be discharged after the distillation.

The simple distillation can be carried out batchwise or continuously.

Suitable polyethers are in particular oligomeric aliphatic polyethers having one or two terminal hydroxyl groups. Preference is given to using polyethylene glycol or polypropylene glycol, particularly preferably polyethylene glycol, in each case with an average molar mass in the range from 200–3000 daltons, preferably in the range from 300–600 daltons, particularly preferably with an average molar mass of 400 daltons.

In the process according to the invention, the amount of polyether that is added can be varied within a relatively wide range. In general, it is between 0.01 and 10 times the amount (w/w=weight by weight) of the diluent-free crude product. The amount of polyether is preferably between 0.1 and 4 times the amount (w/w) of the crude product, particularly preferably between 0.15 and 0.4 times the amount (w/w) of the crude product.

The polyethers used according to the invention are known and commercially available.

In the process according to the invention, the temperature of the distillation bottom can be varied within a relatively wide range. In general, the process is carried out between 60° C. and 150° C., preferably at bottom temperatures between 70° C. and 120° C., particularly preferably between 90° C. and 110° C.

The process according to the invention is carried out under reduced pressure. The distillation pressure is preferably in the range between 0.5 mbar and 10 mbar. The process is particularly preferably carried out between 1 mbar and 4 mbar.

CCMT can be prepared, for example, by the processes described in EP-B 0 446 913 and EP-B 0 763 531. The resulting crude product is initially freed of any diluent that may still be present. The process according to the invention then generally involves adding an oligomeric polyether, then reducing the pressure and distilling the CCMT at the appropriate temperature. However, according to the invention, it is also possible to add the oligomeric polyether even before removing any residual diluent from the synthesis.

If the process according to the invention is carried out continuously, the diluent is removed in a first distillation stage and the CCMT-containing distillation bottom is passed to a second distillation stage where CCMT is distilled off once the pressure has been reduced. In the process according to the invention, the oligomeric polyether can be added either in the first stage or in the second stage.

If the process according to the invention is carried out batchwise, the diluent-containing crude product is admixed with oligomeric polyether. Subsequently, the diluent is removed first, the pressure is then reduced and the CCMT is distilled.

CCMT is used, for example, as an intermediate in the preparation of insecticides (cf. EP-A 0 376 279).

EXAMPLE

Synthesis 500 g (3.74 mol) of 2-chloroallyl isothiocyanate are dissolved in 1250 g of acetonitrile. At 10–15° C., 282 g (3.98 mol) of chlorine are introduced, and the mixture is stirred at 20–25° C. for 2 hours. The mixture is then degassed at 30–35° C. under reduced pressure.

This gives 1944 g of a 29.3% strength solution (GC, internal standard) of CCMT in acetonitrile (yield: 91% of theory).

The mixture is divided into two equal parts.

Part a): Distillation Without Additive

The acetonitrile is distilled off under reduced pressure (about 350 mbar), and the pressure is then reduced to 0.6–0.7 mbar and CCMT is distilled off at a top temperature of about 75° C., until the bottom temperature reaches 110° C.

This gives 263.1 g of an orange-yellow distillate (94.3% pure, GC, internal standard).

Yield: 87% of theory, based on the amount used in the distillation.

The black bottom (41.2 g), which solidifies in a glass-like manner on cooling, has a content of 5.9% (GC, internal standard) of CCMT, corresponding to a theoretical yield of a further 0.9%.

Part b): Distillation with Addition of Polyether

The acetonitrile is distilled off under reduced pressure (about 350 mbar), and 43 g of polyethylene glycol of an average molar mass of 400 are then added to the crude CCMT.

The pressure is reduced further to 1–2 mbar and CCMT is distilled off at a top temperature of about 75° C., until the bottom temperature reaches 110° C.

This gives 268.2 g of CCMT as a virtually colourless distillate of a purity of 98.5% (GC, internal standard).

Yield: 93% of theory, based on the amount used in the distillation.

The black bottom (79.1 g) remains liquid even at room temperature. It has a content of 13.7% (GC, internal standard) of CCMT, corresponding to a theoretical yield of a further 3.8%.

What is claimed is:

1. A process for purifying 2-chloro-5-chloromethylthiazole comprising distilling crude 2-chloro-5-chloromethylthiazole under reduced pressure in the presence of an oligomeric polyether.

2. A process according to claim 1 wherein the polyether is polyethylene glycol or polypropylene glycol.

3. A process according to claim 2 wherein the polyether has an average molar mass between 200 and 3000 daltons.

4. A process according to claim 2 wherein the polyether has an average molar mass between 300 and 600 daltons.

5. A process according to claim 2 wherein the polyether has an average molar mass of 400 daltons.

6. A process according to claim 1 wherein the polyether has an average molar mass between 200 and 3000 daltons.

7. A process according to claim 1 wherein the polyether has an average molar mass between 300 and 600 daltons.

8. A process according to claim 1 wherein the polyether has an average molar mass of 400 daltons.

9. A process according to claim 1 wherein the distillation is carried out at a pressure between 0.5 mbar and 10 mbar.

10. A process according to claim 1 wherein the distillation is carried out at a pressure between 1 mbar and 4 mbar.

11. A process according to claim 1 wherein the distillation is carried out at a temperature between 60 and 150° C.

12. A process according to claim 1 wherein the distillation is carried out at a bottom temperature between 70 and 120° C.

13. A process according to claim 1 wherein the amount of the polyether is between 0.01 and 10 times the weight-by-weight amount of a diluent-free crude 2-chloro-5-chloromethylthiazole.

14. A process according to claim 1 wherein the amount of the polyether is between 0.1 and 4 times the weight-by-weight amount of a diluent-free crude 2-chloro-5-chloromethylthiazole.

* * * * *